US 6,673,043 B1

(12) United States Patent
Landesberg

(10) Patent No.: US 6,673,043 B1
(45) Date of Patent: Jan. 6, 2004

(54) CANNULATION DEVICE AND APPARATUS

(75) Inventor: Amir Landesberg, Haifa (IL)

(73) Assignee: Levram Medical Devices, Ltd., Nesher (IL)

( * ) Notice: Subject to any disclaimer, the term of this patent is extended or adjusted under 35 U.S.C. 154(b) by 137 days.

(21) Appl. No.: 09/712,431

(22) Filed: Nov. 14, 2000

(51) Int. Cl.[7] ............................................. A61M 29/00
(52) U.S. Cl. ................... 604/106; 604/104; 604/164.09
(58) Field of Search .................. 604/104, 105, 604/106, 107, 108, 109, 164.09

(56) References Cited

U.S. PATENT DOCUMENTS

| 212,600 | A | * | 2/1879 | Harz ........................... 604/104 |
| 237,032 | A | * | 1/1881 | Mayer ......................... 604/104 |
| 297,263 | A | * | 4/1884 | Hunt ........................... 604/104 |
| 1,943,110 | A | * | 9/1932 | Corbett ....................... 604/104 |
| 3,995,617 | A | | 12/1976 | Watkins et al. |
| 4,014,317 | A | | 3/1977 | Bruno |
| 4,518,327 | A | | 5/1985 | Hackman |
| 4,755,171 | A | | 7/1988 | Tennant |
| 4,769,031 | A | | 9/1988 | McGough et al. |
| 5,271,385 | A | | 12/1993 | Bailey |
| 5,571,215 | A | | 11/1996 | Sterman et al. |
| 5,613,937 | A | | 3/1997 | Garrison et al. |
| 5,682,906 | A | | 11/1997 | Sterman et al. |
| 5,690,606 | A | | 11/1997 | Slotman |
| 5,713,951 | A | | 2/1998 | Garrison et al. |
| 5,718,725 | A | | 2/1998 | Sterman et al. |
| 5,728,151 | A | | 3/1998 | Garrison et al. |
| 5,814,005 | A | | 9/1998 | Barra et al. |
| 5,814,097 | A | * | 9/1998 | Sterman et al. ............... 606/99 |
| 5,843,088 | A | | 12/1998 | Barra et al. |
| 5,846,194 | A | | 12/1998 | Wasson et al. |
| 5,897,490 | A | | 4/1999 | Fox et al. |
| 5,972,030 | A | | 10/1999 | Garrison et al. |
| 6,113,535 | A | | 9/2000 | Fox et al. |

FOREIGN PATENT DOCUMENTS

EP 0 405 749 A1 6/1992

* cited by examiner

Primary Examiner—Manuel Mendez
(74) Attorney, Agent, or Firm—Herbert Dubno

(57) ABSTRACT

An incision in a ventricle wall is spread without applying axial force to the ventricle wall by inserting an array of pins and then spreading that array while a cannula is inserted along the track formed by the pins.

20 Claims, 9 Drawing Sheets

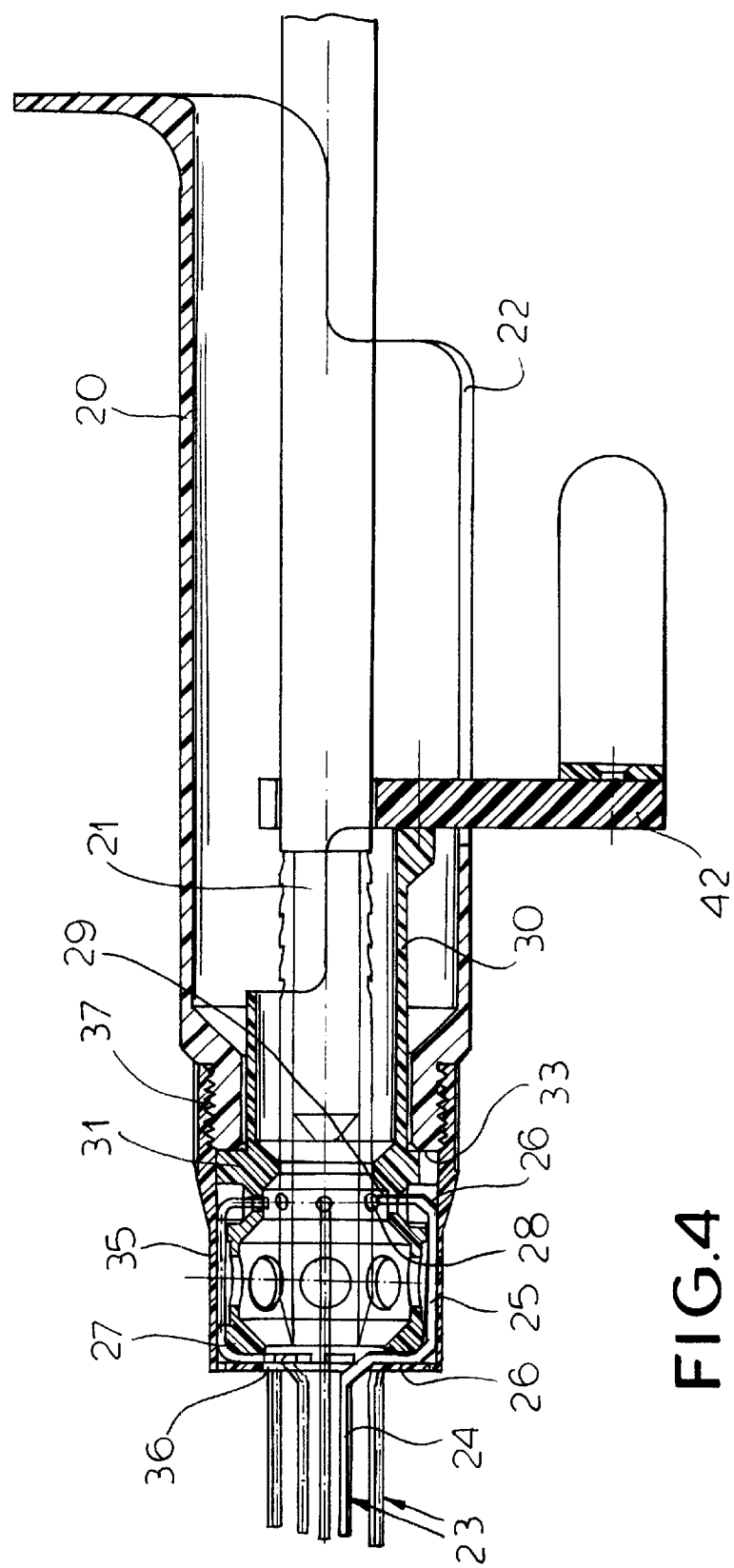

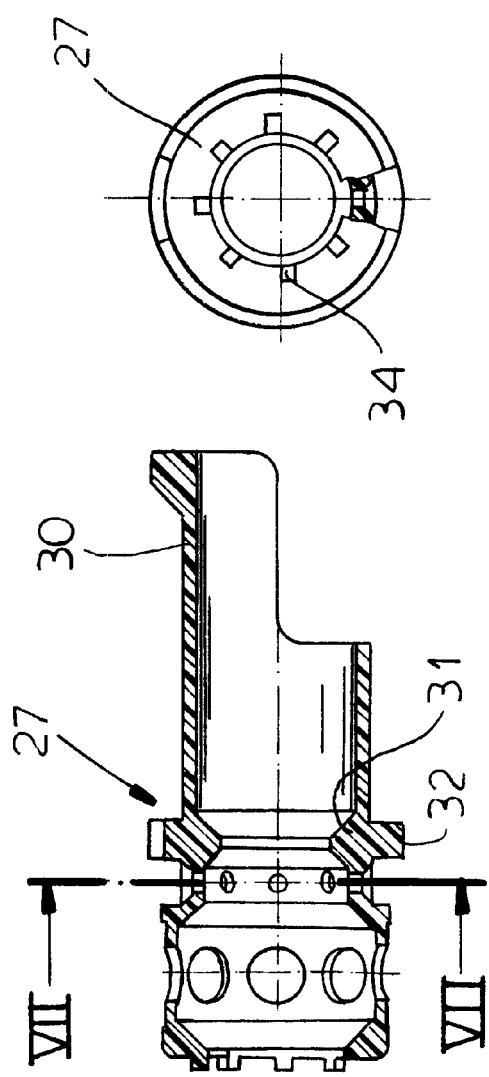
FIG.6
FIG.5
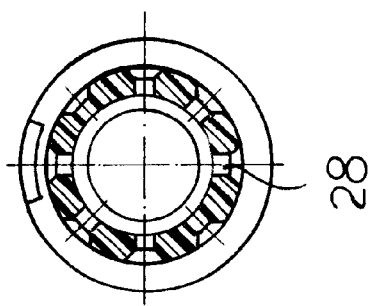
FIG.7

CANNULATION DEVICE AND APPARATUS

FIELD OF THE INVENTION

My present invention relates to a cannulation device and method and, more particularly, to a device which permits the introduction of a cannula into tissue of a patient, especially cardiac tissue and most specifically for ventricular cannulation as may be required for the installation of ventricular-assist devices which augment cardiac blood circulation.

BACKGROUND OF THE INVENTION

Cardiac-assist devices can support circulation in cases of severe heart failure. Cardiac-assist devices, also referred to as ventricular-assist devices (VAD) draw blood from the left ventricle and eject it into the aorta. The blood is withdrawn through a tube or cannula introduced into the left ventricle, is displaced by a pump and is ejected through a tube which is inserted into the aorta.

The insertion of the tube into, for example, the ventricle through the cardiac tissue is referred to as ventricular cannulation and it is such introduction of the cannula that is the concern of this invention.

It should be noted that the implantation of a ventricular-assist device can be quite costly because the surgical procedure also requires intensive care required over a period of, say, twenty days. The high cost, long recovery time and related factors reduce the utility of the procedure for many patients. The assist device itself can be quite expensive in addition.

In addition to the high cost, conventional techniques involve major intervention and a traumatic procedure at lesat in part because of the need to connect the patient to a heart/lung machine. The latter technique is widely used but prolongs the duration of the surgery and increases the recovery time and the complexity of the equipment required for surgery. This major intervention increases the mortality and morbidity.

Conventional techniques for ventricular cannulation have involved piercing the cavity wall with a sharp tube over which the cannula can be fitted. Alternatively, a piece of tissue may be cut out of the ventricle with a coring knife. Both techniques require supporting the heart muscle which is pierced by the tool against the axial force applied against to the ventricle wall and cannot easily be accomplished while the heart is beating and full of blood.

The bleeding from the site can be extensive and can prevent the surgeon from seeing the action at the cardiac muscle wall. To assist having to handle the bleeding heart, the cardiac/pulmonary bypass approach has been used.

OBJECTS OF THE INVENTION

It is, therefore, the principal object of the present invention to provide an improved device for beating-heart cannulation, especially ventricular cannulation, that is simple to operate, inexpensive and eliminates the need to connect the patient to a heart/lung bypass circulation and thereby obviates the drawbacks described.

Another object is to provide an improved cannulation device which simplifies the surgical procedures involved, especially in cannulation for ventricular-assist devices, reduces complications in such surgical procedures and minimizes morbidity, mortality and cost.

It is also an object of this invention to provide an improved cannulation method whereby disadvantages of earlier cannulation systems are obviated.

SUMMARY OF THE INVENTION

I have found that the disadvantages of earlier systems with respect to the introduction of a cannula into tissue and especially the ventricular cannulation can be eliminated by eliminating the axial forces which are applied by the cannulation device implementation to the tissue while guiding the cannula into place, and, therefore, by spreading an incision in the tissue purely radially for this purpose. The term "cannulation device" when broadly used in this description and the appended claims can include the surgical tools, therapeutic devices (balloons), diagnostic sensors, optical devices and any equipment for automating and/or monitoring the procedures described.

According to the invention, the procedure involves inserting into an incision in the tissue a narrow array of members which are then pressed outwardly without applying an axial component of force to the tissue, thereby spreading the incision and forming a circular opening while guiding within that array of members a cannula into the incision. Upon retraction of the members, therefore, the cannula is seized by the edges of the opening or incision as they naturally elastically contract around the cannula. The device can be anchored to the tissue by subsequent suturing to prevent it from sliding in or out.

More particularly, the cannulation device for the purposes described can comprise
  a handle;
  a plurality of pins in a circular array projecting from an end of the handle;
  an actuator on the handle operatively connected with the pins for spreading the array from a narrow configuration in which the pins are insertable through an incision in tissue in which cannulation is to be effected into a wide position in which the tissue is radially and elastically spread at the incision; and
  a cannula in the handle insertable through the array in the wide position for anchoring in the tissue by contraction of the tissue around the incision.

According to a feature of the invention the pins are formed as generally linear shanks on respective wire springs, each of the wire springs having a pivot portion parallel to the respective shank but offset laterally therefrom and a connecting portion between the respective shank and the respective pivot portion, the actuator including a sleeve provided with formations engaging the wire springs and rotating the connecting portions about axes of the pivot portions to radially displace the shanks between the positions.

The pivot portions are fixed on the handle whereby each of the wire springs is twisted about the respective axis by the respective formation, thereby torsionally stressing the respective wire spring, the shanks returning toward the narrow position by spring force resulting from the torsional stressing of the wire springs upon release of the actuator.

The actuator can have a lever projecting laterally form the handle and enabling rotation of the sleeve by a hand of a user holding that handle. The handle itself can be hollow and provided with a cut-out through which the cannula can be pressed through the array of pins into the opening by a finger of the user.

A cover can be fitted over the sleeve and the pivot portions of the wire spring at the end of the handle and can have an opening through which the shanks can project. The cannula, in turn, can have a tapered end adapted to lie in a body organ and an opposite end which can be connected to, for example, the intake side of the ventricular assist device.

It has been found to be advantageous to provide the formations as projections on an end of the sleeve. The array should include at least eight pins or shanks and the sleeve can project from an end of the handle and can have a cylindrical extension received in the handle. The sleeve and the handle can be connected by a rib-and-groove connection for axially fixing the sleeve to the handle.

The cannulation method can comprise the steps of:

(a) forming an incision in tissue into which a cannula is to be introduced;

(b) inserting into the incision a narrow array of pins;

(c) spreading the pins into a wide array to thereby radially expand the incision elastically and form an opening without axially stressing the tissue;

(d) inserting a cannula into the opening within the wide array of pins thereby plugging the opening; and (e) withdrawing the pins from the tissue and leaving the cannula in the opening to eliminate bleeding or spilling of visceral fluids whereby the cannula is particularly retained in the tissue by elastic contraction of the tissue around the cannula.

The tissue is usually a ventricle wall and the cannula is inserted into a ventricle of the patient. The cannula is pushed into the opening simultaneously with the widening thereof by the pin. The cannula can thus be inserted into a beating heart without removal of the tissue from the ventricle wall.

With the system of the invention, once the incision is made, the only forces applied to the cavity wall are radial forces which spread the orifice to the diameter required by the cannula and no forces are exerted in the axial or inward direction. During the axial movement of the cannula, it is guided in a track formed by the shanks of the pins. The synchronous radial opening of the orifice and inward movement of the cannula seals the opening in the wall. The synchronous action of spreading the orifice and inserting the cannula can easily be accomplished by the single hand of a surgeon, but may be synchronized by a computer-controlled system operating respective actuators for spreading the opening and inserting the cannula. The pins preferably are of circular or semicircular cross section but can have other shapes as well. The shapes of the springs can also be varied and the shanks can be rigid or flexible.

BRIEF DESCRIPTION OF THE DRAWING

The above and other objects, features, and advantages will become more readily apparent from the following description, reference being made to the accompanying drawing in which:

FIG. 4 is a cross sectional view through a manual device for cannulation of the ventricle;

FIG. 5 is a detail section of a portion of the device;

FIG. 6 is an end view thereof;

FIG. 7 is a cross sectional view taken along the line VII—VII of FIG. 5;

SPECIFIC DESCRIPTION

Figure 1:
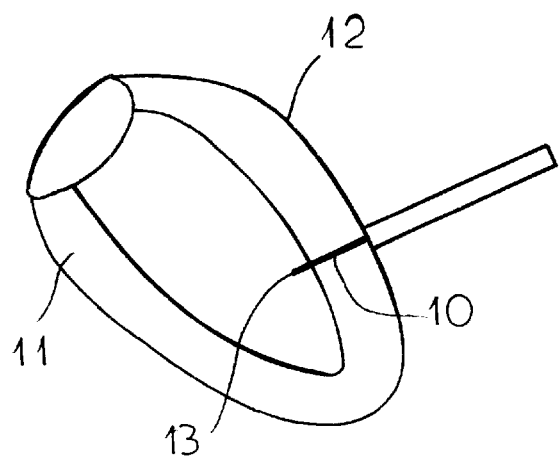
FIG. 1 is a diagram showing an initial step in the cannulation of a ventricle in accordance with the invention.
Figure 2:
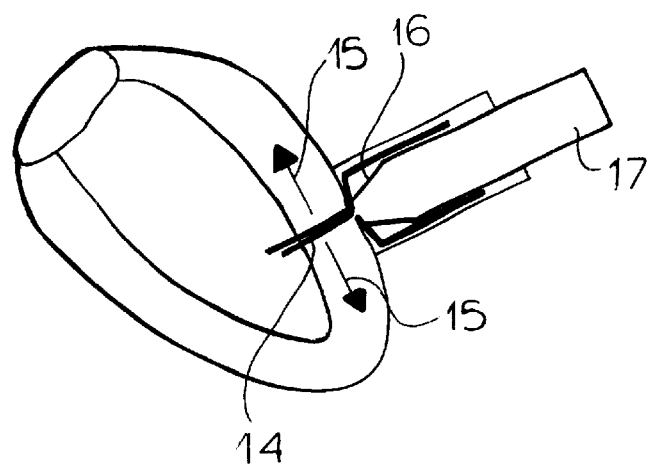
FIG. 2 is a diagram similar to FIG. 1 showing a second step in the process.
Figure 3:
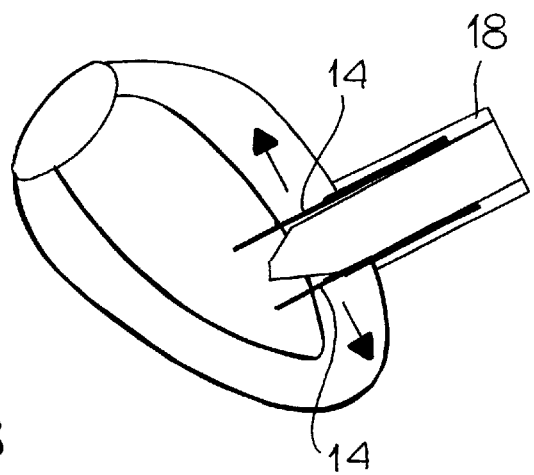
FIG. 3 is a diagram similar to FIGS. 1 and 2 illustrating a third step in the process.

According to the invention, an incision 10 is made in a beating heart 11 through a ventricle wall 12 thereof by a scalpel 13 and without removal of the tissue of this wall.

Then an array of pins 14 is inserted into the incision and spread outwardly to radially spread the edges of the incision as represented by the arrows 15 simultaneously with the advance of a tapered end 16 of a cannula 17 along the track formed by the pins 14 into the incision. Once the cannula is lodged in the incision, the pins are withdrawn, e.g. on a handle 18 in which the pins may be held.

The device thus creates radial forces only on the tissue and the tissue stretches and opens the circular track without imposing any forces in the inward direction. No inward compressive forces are thus exerted on the ventricle and no distortion of the lumen can occur. Since the tissue is elastically pressed away from the incision, radial elasticity of the tissue holds the cannula firmly and the elastic engagement of the pins prevents the ventricle from slipping away from the device. The ventricle wall can then be sutured around the cannulation for reinforcement. Cannulation is thus effected with a minimum invasive approach and can be effected through a small opening in the chest wall (Minimally invasive procedure).

Bleeding during cannulation is minimized because the ventricle wall is plugged by the advancing cannula as it follows the radial opening. The setting of the cannula from the time of insertion of the pins into the incision can take less than a second and the skill required is minimal.

As can be seen from FIGS. 4–7, the device itself can comprise a handle 20 which is hollow to enable the cannula 21 to be inserted. A slot 22 in a lateral wall of the handle enables a finger to press the cannula into place through the track formed by the pins 23.

Each of the pins 23 is a bent wire spring having a shank 24 parallel to a pivot portion 25 of the spring which is connected to the shank by a transverse portion 26 and is offset outwardly therefrom. The spring pins 23 are held within the handle 20 at 26 and thus can be bent about the portion 25, i.e. the spring twisted, for deflection of the shanks 24 outwardly. To actuate the device, a sleeve 27 (see also FIG. 5) is provided by and with the holes 28 into which bent legs 29 of the spring can be inserted. A cylindrical portion 30 is connected to the sleeve by a portion 31 having an outwardly-extending rib 32 engageable in a groove 33 of the handle 20.

At the front end of the sleeve 27 are projections 34 which serve to twist the individual springs as will be described in connection with FIGS. 9–13. A casing 35 surrounds the sleeve and is formed with an opening 36 through which pins emerge, the casing 36 also protecting the springs and being fitted at 37 onto an end of the housing 20.

Figure 8:
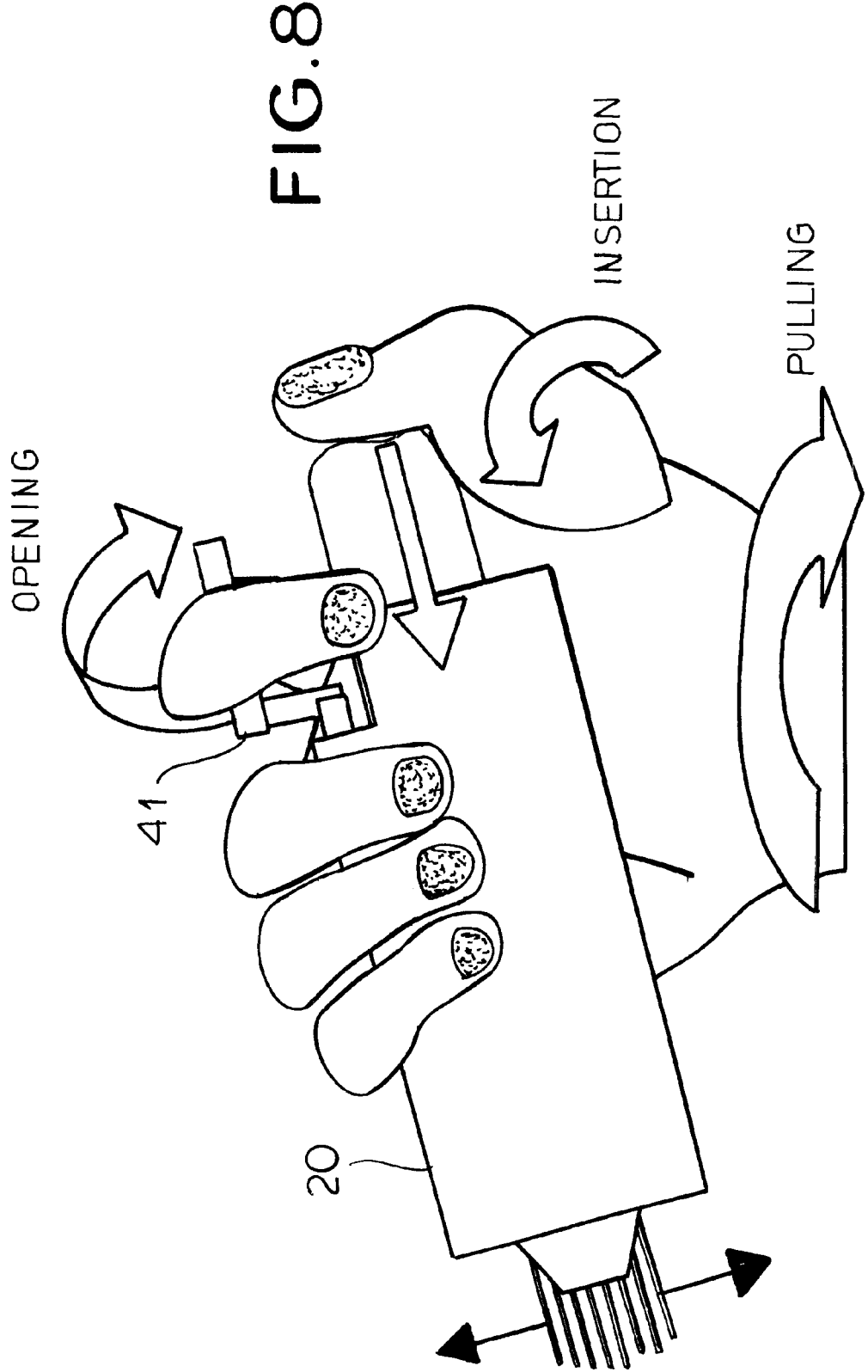
FIG. 8 is a diagram illustrating manual synchronization.
Figure 9:
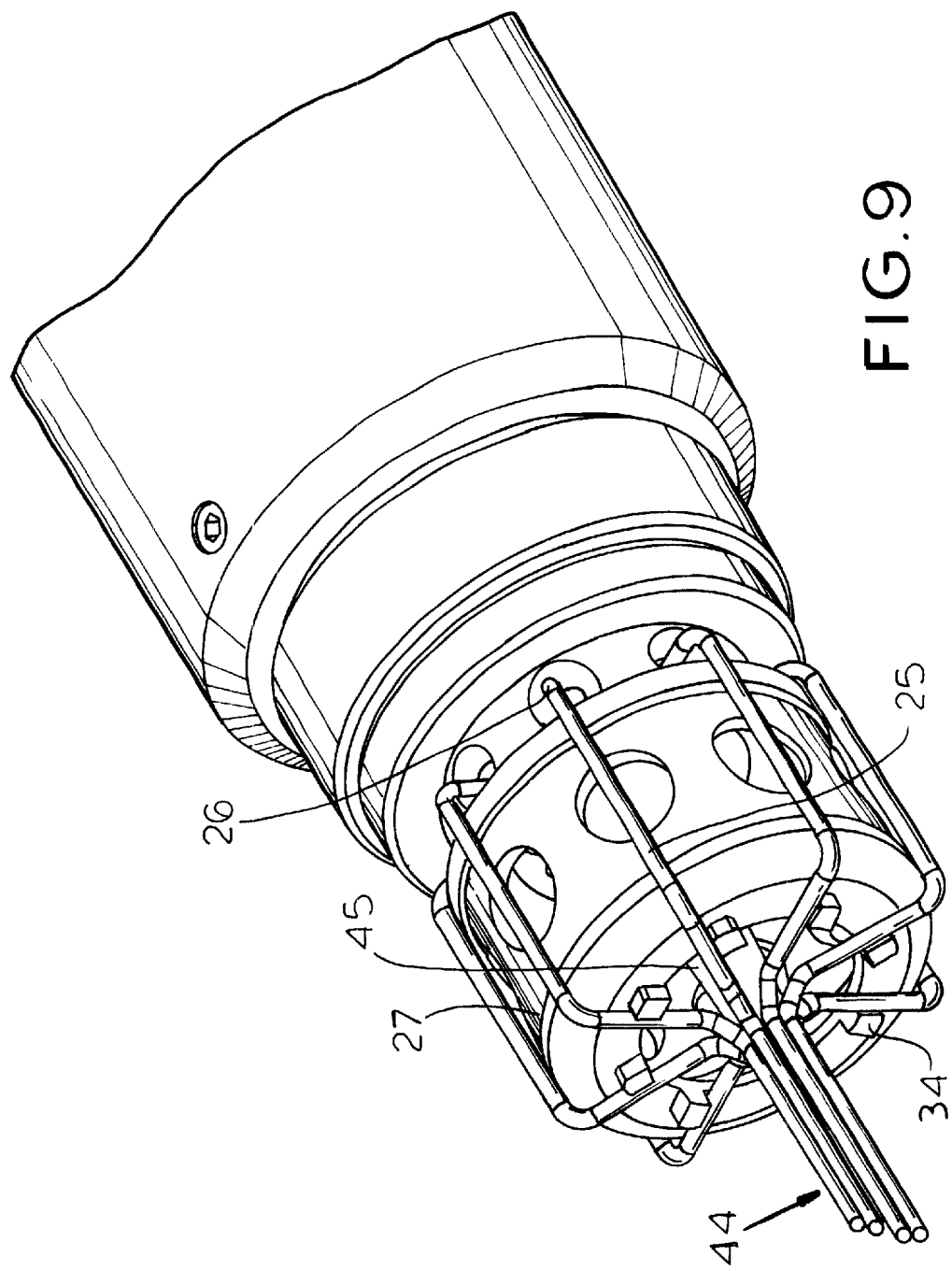
FIG. 9 is a detail perspective view showing the apparatus in the closed position.
Figure 10:
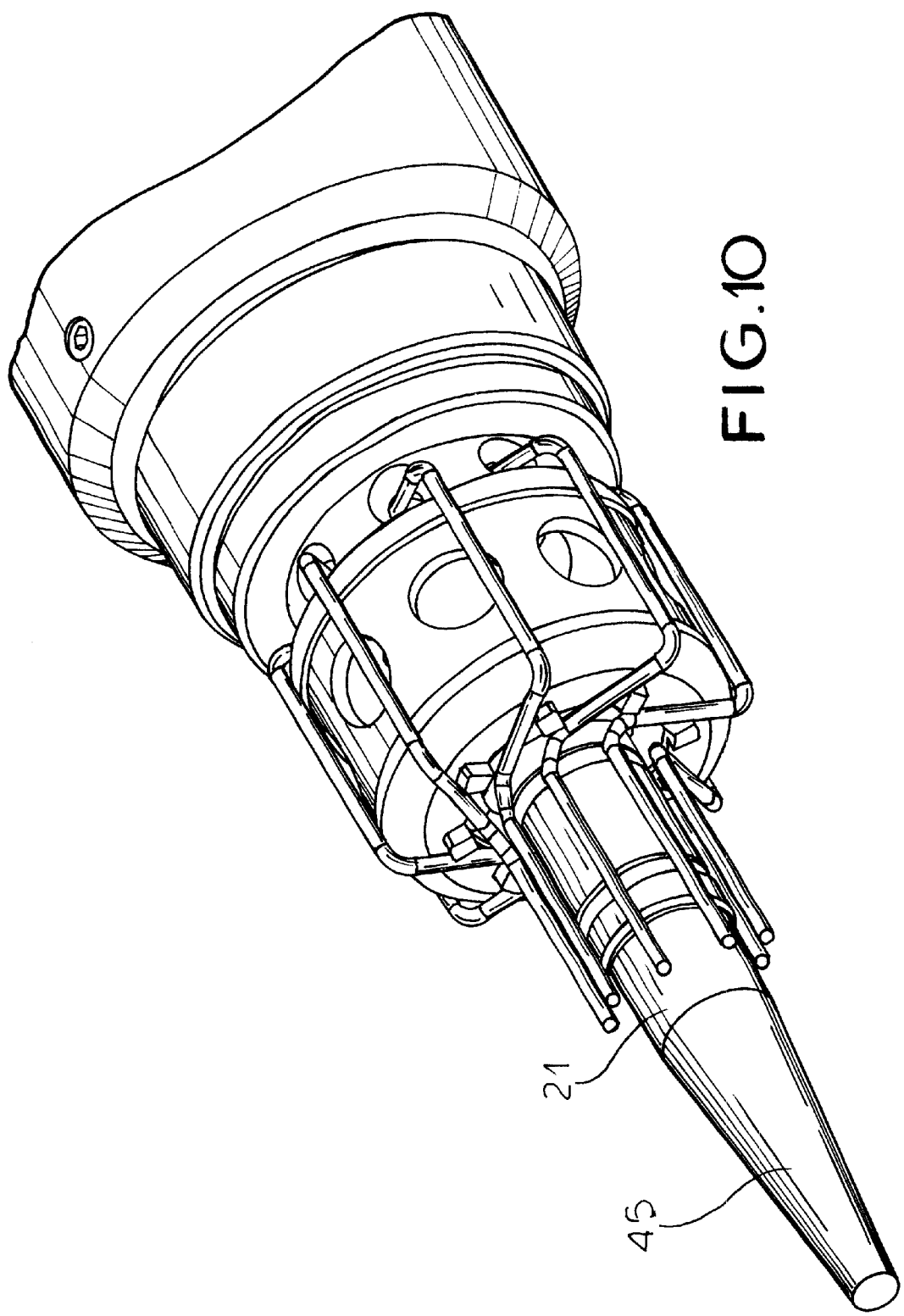
FIG. 10 is a view similar to FIG. 9 showing the open position.
Figure 11:
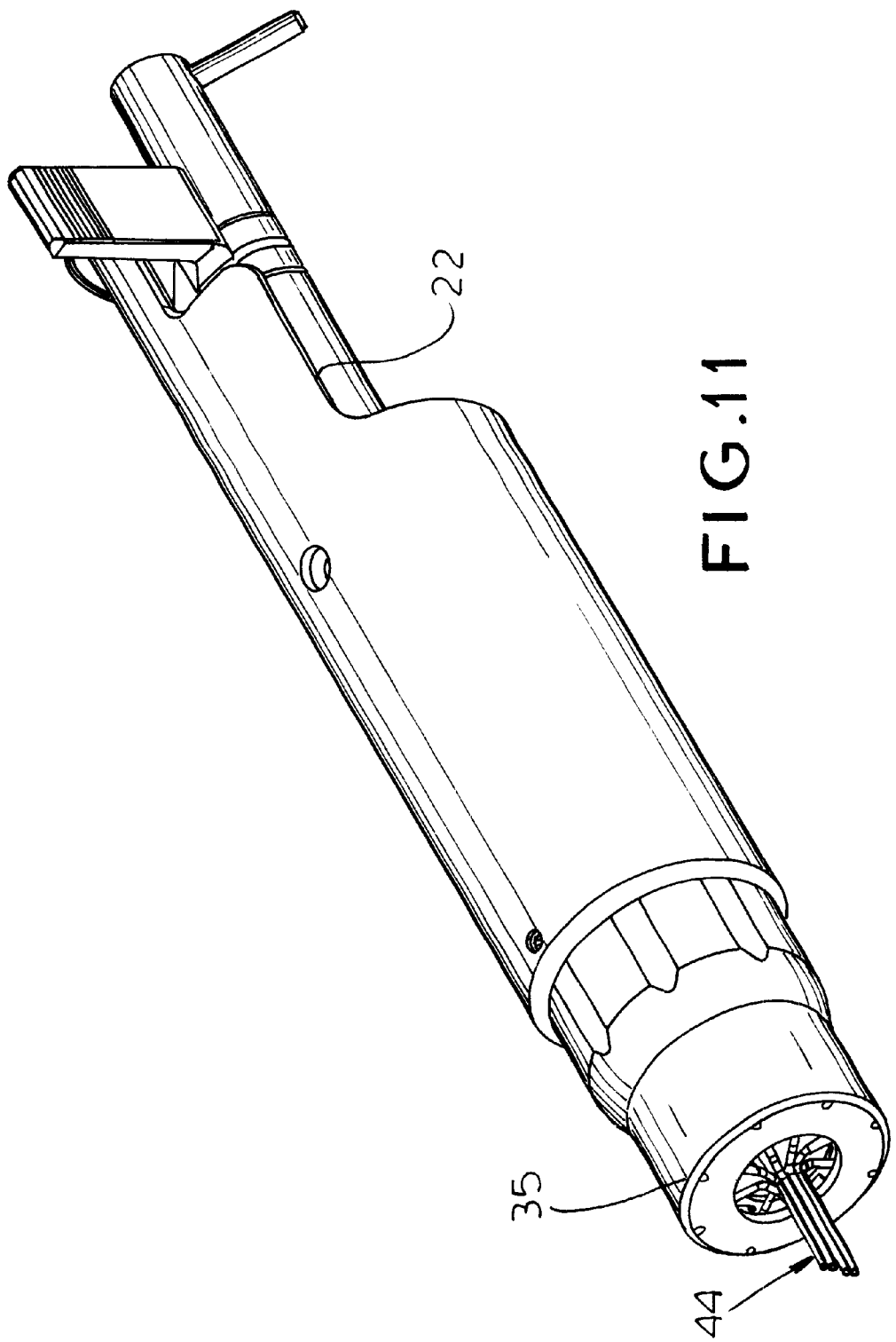
FIG. 11 is a perspective view of the device in the closed position.
Figure 12:
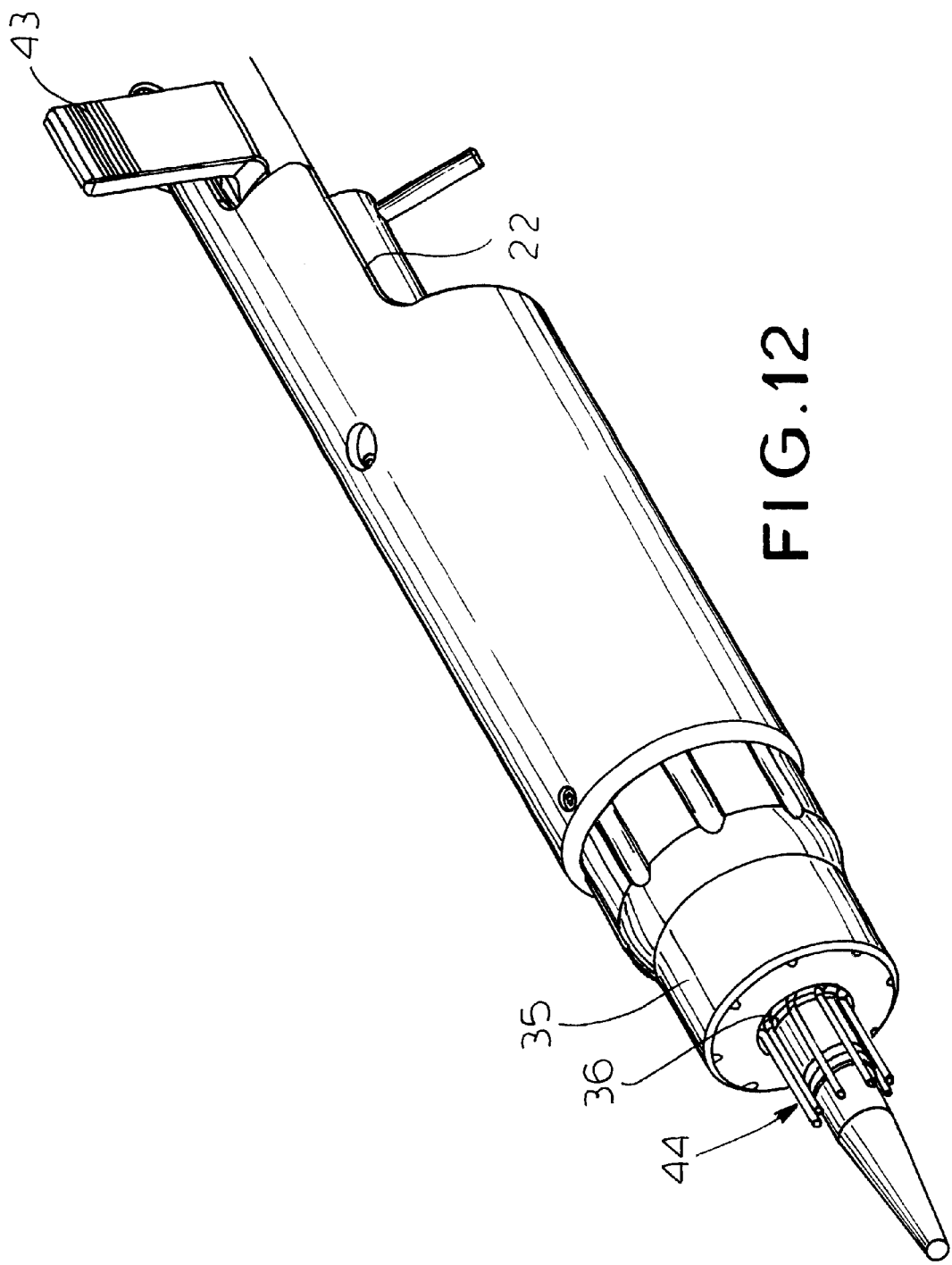
FIG. 12 is a perspective view of the device showing the open position.
Figure 13:
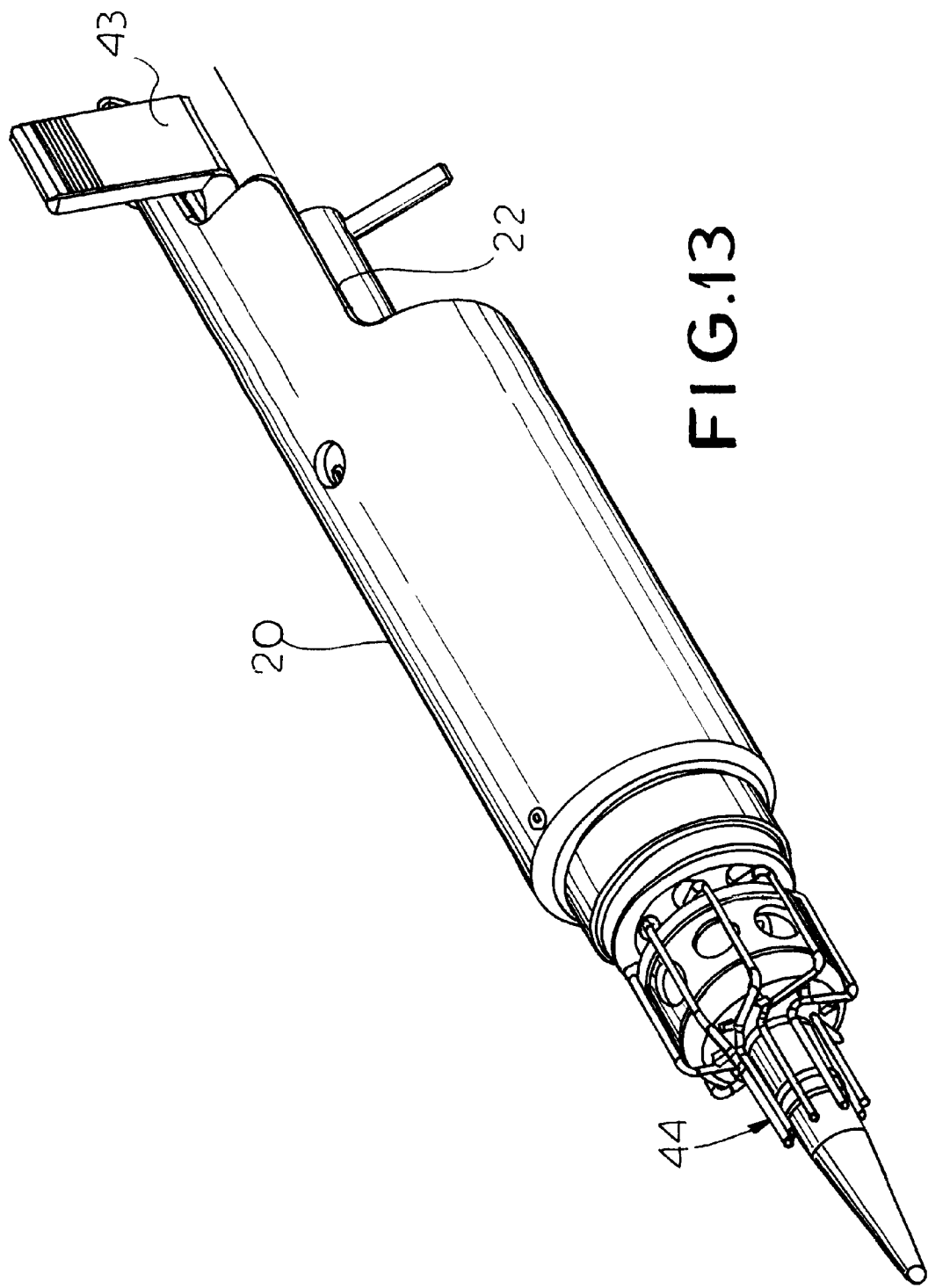
FIG. 13 is a view similar to FIG. 12 but with the front casing removed.

The cylindrical portion 30 is provided with a lever 41 in FIG. 8 and 42 in FIG. 4 or 43 in FIGS. 11–13, which serves to rotate the sleeve.

When the array of pins, which may be eight in number or more is in its closed position, it is inserted in the incision. The closed array has been shown at 44 in FIG. 9 and the tapered tip 45 of the cannula is there seen directly behind the array.

When the sleeve 27 is rotated, the projections 34 twist the pins about the axes of the offset portions 25 which are fixed at 26 so that the array is spread (FIG. 10) simultaneously with the advance of the cannula 21 with its tapered tip 45.

From FIGS. 11 and 12, it is clear that a casing from cover 35 surrounds the sleeve 27 and the portions of the springs mounted thereon while the pins 44 pass through the opening 36 in that casing. The movement of the cannula in the lateral wall 22 is visible by comparing FIGS. 11 and 12. The simultaneous spreading of the pins and insertion of the cannula has been illustrated diagrammatically in FIG. 8 and, once the cannula is set, of course, the pins can be pulled out.

FIG. 13 shows the device with the casing removed.

Advantageously, the diameter of the array of pins in the closed position is about 2 mm and the perimeter smaller than the circumference of the scalpel blade which forms the incision in the ventricle wall tissue. The incision is made through the thickness of the cavity wall but causes no bleeding because residual stresses in the ventricle wall tend to seal the puncture site.

The rotation of the handle, by flexion of the second finger (see FIG. 8) which rotates the sleeve about its axis through about 15°, spreads the array which should be composed of at least eight pins to a maximum radial opening which can be, say, 25 mm. Simultaneously with the widening of the track defined by the array of pins, the cannula is pushed forward by the thumb of the operator and the synchronization is effected by coordinating the action of the two fingers.

The cannulation method and device of the invention have a number of advantages over prior cardiac cannulation methods including elimination of the need for circulatory bypass or the use of a cardiopulmonary apparatus and the lack of need to empty the blood from the heart.

There is no need to arrest the heart and the method and apparatus work with a beating heart. The system operates with a relatively small chest opening and hence a minimum invasive approach since there is no need to insert both hands into the thorax to grab the heart.

The system is capable of rapid insertion of the cannula, normally taking less than 15 seconds, not including the thoracotomy and suturing.

The insertion of the cannula without axial force is along a well-defined track radially opened through the tissue and the cannula is anchored by the radial forces of contraction of the tissue to form a tight anchor. There is no need to seize the tissue during cannulation.

Axial forces that may push the tissue inward and distort the geometry of the cavity are precluded and thus there are no changes in the cardiac hemodynamics during and after cannulation.

No ventricle mass is removed and since the tissue retains its integrity, it readily seals by contraction so that there is better recovery and tissue repair once the cannula is pulled out.

I claim:

1. A cannulation device comprising:
   a handle;
   a plurality of pins in a circular array projecting from an end of said handle;
   an actuator on said handle operatively connected with said pins for spreading said array from a narrow configuration in which said pins are insertable through an incision in tissue in which cannulation is to be effected into a wide position in which said tissue is radially and elastically spread at said incision; and
   a cannula in said handle insertable through said array in said wide position for anchoring in said tissue by contraction of said tissue around said incision, said pins being formed as generally linear shanks on respective wire springs, each of said wire springs having a pivot portion parallel to the respective shank but offset laterally therefrom and a connecting portion between the respective shank and the respective pivot portion, said actuator including a sleeve provided with formations engaging said wire springs and rotating said connecting portions about axes of said pivot portions to radially displace said shanks between said positions.

2. The cannulation device defined in claim 1 wherein said pivot portions are fixed on said handle whereby each of said wire springs is twisted about the respective axis by the respective formation, thereby torsionally stressing the respective wire spring, said shanks returning toward said narrow position by spring force resulting from the torsional stressing of said wire springs upon release of said actuator.

3. The cannulation device defined in claim 2 wherein said actuator has a lever projecting laterally from said handle and enabling rotation of said sleeve by a finger of a hand of a user holding said handle.

4. The cannulation device defined in claim 3 wherein said handle is hollow and is provided with a cutout through which said cannula can be pressed through said array.

5. The cannulation device defined in claim 4, further comprising a cover fitted over said sleeve, said pivot portions of said wire springs and an end of said handle, said cover having an opening through which said shanks project.

6. The cannulation device defined in claim 5 wherein said cannula has a tapered end adapted to lodge in a body organ and inserted through said array, and an opposite end for receiving an extension tube.

7. The cannulation device defined in claim 5 wherein said formations are projections on an end of said sleeve.

8. The cannulation device defined in claim 5 wherein said array comprises at least eight shanks.

9. The cannulation device defined in claim 5 wherein said sleeve projects from an end of said handle and has a cylindrical extension received in said handle, one of said handle and said extension being formed with a groove and the other of said handle and said extension being formed with a rib received in said groove for axially fixing said sleeve to said handle.

10. A ventricular cannulation device comprising:
    a plurality of pins forming a narrow circular array and insertable in an incision in a ventricle wall;
    a cannula in line with said array of pins; and
    an actuator for simultaneously radially spreading said array to spread said incision and advancing said cannula through said array along a track formed within said array of pins, thereby lodging said cannula in the ventricle wall, said pins being formed as generally linear shanks on respective wire springs, each of said wire springs having a pivot portion parallel to the respective shank but offset laterally therefrom and a connecting portion between the respective shank and the respective pivot portion, said actuator including a sleeve provided with formations engaging said wire springs and rotating said connecting portions about axes of said pivot portions to radially displace said shanks.

11. The cannulation device defined in claim 10 wherein said pivot portions are fixed whereby each of said wire springs is twisted about the respective axis by the respective formation, thereby torsionally stressing the respective wire spring, said shanks returning toward said narrow position by spring force resulting from the torsional stressing of said wire springs upon release of said actuator.

12. The cannulation device defined in claim 11 wherein said actuator has a lever enabling rotation of said sleeve by a finger of a hand of a user.

13. The cannulation device defined in claim 12, further comprising a cover fitted over said sleeve, said pivot portions of said wire springs and an end of said handle, said cover having an opening through which said shanks project.

14. The cannulation device defined in claim 13 wherein said cannula has a tapered end adapted to lodge in a body organ and inserted through said array, and an opposite end for receiving an extension tube.

15. The cannulation device defined in claim 14 wherein said formations are projections on an end of said sleeve.

16. The cannulation device defined in claim 14 wherein said array comprises at least eight shanks.

17. A cannulation method comprising the steps of:
(a) forming an incision in tissue into which a cannula is to be introduced;
(b) inserting into said incision a narrow array of pins formed as generally linear shanks on respective wire springs, each of said wire springs having a pivot portion parallel to the respective shank but offset laterally therefrom and a connecting portion between the respective shank and the respective pivot portion;
(c) spreading said pins into a wide array by engaging the wire springs with formations on an actuator sleeve to rotate the connecting portions about axes of said pivot portions to thereby radially expand said incision elastically and form an opening without axially stressing the tissue;
(d) inserting a cannula into said opening within said wide array of pins thereby plugging said opening; and
(e) withdrawing said pins from said tissue and leaving said cannula in said opening whereby said cannula is retained in said tissue by elastic contraction of said tissue around said cannula.

18. The method defined in claim 17 wherein said tissue is a ventricle wall and said cannula is inserted into a ventricle of a patient.

19. The method defined in claim 18 wherein said cannula is pushed into said opening simultaneously with widening thereof by said pins.

20. The method defined in claim 19 wherein said cannula is inserted into a beating heart without removal of tissue from the ventricle wall.

* * * * *